United States Patent [19]

Desreux et al.

[11] Patent Number: 5,358,704

[45] Date of Patent: Oct. 25, 1994

[54] HEPATOBILIARY TETRAAZAMACROCYCLIC MAGNETIC RESONANCE CONTRAST AGENTS

[75] Inventors: Jean F. Desreux, Angleur, Belgium; Michael F. Tweedle, Princeton, N.J.; Peter C. Ratsep, Hamilton Square, N.J.; Thomas R. Wagler, Princeton, N.J.; Edmund R. Marinelli, Lawrenceville, N.J.

[73] Assignee: Bristol-Myers Squibb, Princeton, N.J.

[21] Appl. No.: 129,870

[22] Filed: Sep. 30, 1993

[51] Int. Cl.$^5$ ............... A61B 5/055; C07D 245/00
[52] U.S. Cl. ........................ 424/9; 436/173; 128/653.4; 514/186; 514/836; 534/16; 540/465; 540/473
[58] Field of Search ........... 540/473, 465; 424/9; 436/173; 128/653.4, 654; 514/186, 836; 534/16

[56] References Cited

U.S. PATENT DOCUMENTS

| | | | |
|---|---|---|---|
| 4,880,008 | 11/1989 | Lauffer | 128/654 |
| 4,899,755 | 2/1990 | Lauffer et al. | 128/654 |
| 5,087,696 | 2/1992 | Parker et al. | 540/465 |

FOREIGN PATENT DOCUMENTS 0255471 7/1987 European Pat. Off. .
438206 7/1991 European Pat. Off. .
WO91/10669 7/1991 PCT Int'l Appl. .

OTHER PUBLICATIONS

Gries et al. Chem. Abstracts 116(9):84709s (1991).

*Primary Examiner*—Gary E. Hollinden
*Attorney, Agent, or Firm*—John M. Kilcoyne

[57] ABSTRACT

Novel compounds of the formula

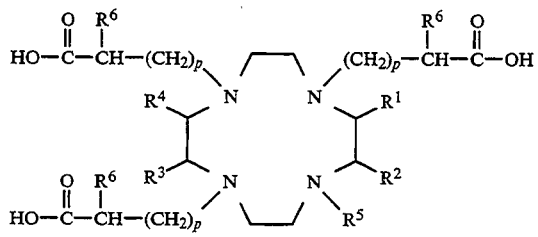

and metal chelates of the compounds are useful particularly for MRI of the hepatobiliary system.

20 Claims, No Drawings

HEPATOBILIARY TETRAAZAMACROCYCLIC MAGNETIC RESONANCE CONTRAST AGENTS

BRIEF DESCRIPTION OF THE INVENTION

In accordance with the present invention, novel compounds are provided. These compounds are useful, for example, as metal-chelating ligands and, in the form of metal complexes, the present compounds are especially useful as diagnostic contrast agents. When the metal in the complex is paramagnetic, the diagnostic contrast agents are suitable for magnetic resonance imaging, and are particularly useful for magnetic resonance imaging (MRI) of the liver and bile ducts.

The compounds of the invention comprise a tetraazacyclododecane macrocycle containing at least one fused cyclohexyl ring, and are represented by the formula I:

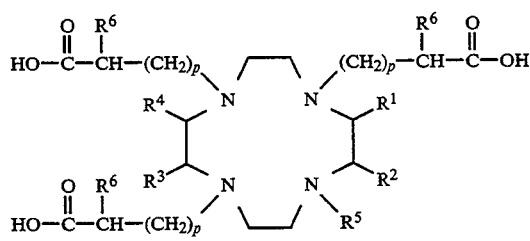

wherein
$R^1$ and $R^2$ and $R^3$ and $R^4$ independently form, together with the carbon atoms in the tetraazacyclododecane macrocycle to which they are attached, a fused fully or partially saturated nonaromatic cyclohexyl ring which may be unsubstituted or substituted by one or more halogen, alkyl, ether, hydroxy or hydroxyalkyl groups, and which may be further fused to a carbocyclic ring, or $R^1$ and $R^2$ are each hydrogen and $R^3$ and $R^4$ form a fused fully or partially saturated non-aromatic cyclohexyl ring as defined above, or $R^1$ and $R^2$ form a fused fully or partially saturated non-aromatic cyclohexyl ring as defined above and $R^3$ and $R^4$ are hydrogen;
$R^5$ is

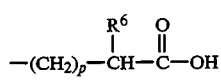

or hydrogen, alkyl, aralkyl, aryl, alkoxy, hydroxyalkyl,

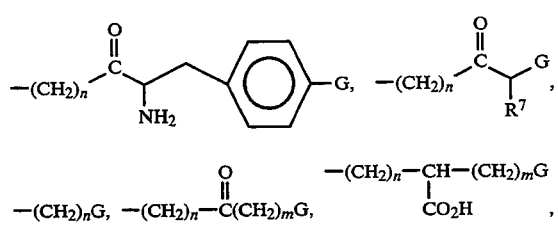

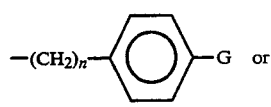

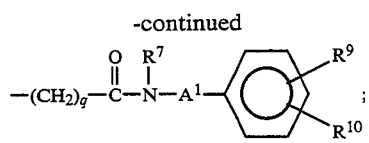

$A^1$ is —(CH$_2$)$_q$—, —(CH=CH)—, —(CH=CH)$_2$— or a single bond; each —(CH$_2$)$_q$— may be independently substituted with alkyl or hydroxyalkyl;
$R^6$ is hydrogen or alkyl;
$R^7$ is hydrogen, hydroxyalkyl, alkoxy, alkyl, aryl or aralkyl;
G is —NH$_2$, —NCS,

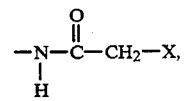

—CO$_2$H, —NHR$^8$, —N(R$^8$)$_2$ or —CN;
$R^8$ is alkyl, hydroxyalkyl,

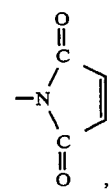

$R^8$ is alkyl, hydroxyalkyl,

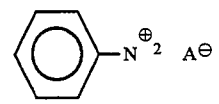

(where A is an anion),

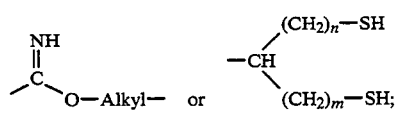

$R^9$ and $R^{10}$ are each independently hydrogen, alkyl, —NO$_2$, —NH$_2$,

or —NR$^7$COR$^6$;
$R^{11}$ is hydrogen, alkyl or hydroxyalkyl;
$R^{12}$ is hydrogen, hydroxyalkyl, alkoxy, alkyl, aryl or aralkyl;
X is chloro, bromo or iodo;
m and n are each independently zero or an integer from one to five;
p is zero or one; and
q is an integer from 1 to 5;
and salts thereof.

DETAILED DESCRIPTION OF THE INVENTION

Listed below are definitions of various terms used in the description of this invention. These definitions apply to the terms as they are used throughout this specification, unless otherwise limited in specific instances, either individually or as part of a larger group.

The terms "alkyl" and "alkoxy" refer to both straight and branched, unsubstituted chains of carbon atoms. Those chains having 1 to 5 carbon atoms are preferred. Methyl and methoxy are the most preferred alkyl and alkoxy groups, respectively.

The term "aryl" refers to phenyl and substituted phenyl. Preferred substituted phenyl groups are those substituted with 1, 2 or 3 halogen, hydroxyl, hydroxyalkyl, alkyl, alkoxy, carbamoyl, carboxamide, acylamino or carboxyl moieties.

"Hydroxyalkyl" refers to straight and branched alkyl groups including one or more hydroxy radicals such as $-CH_2CH_2OH$, $-CH_2CH_2OHCH_2OH$, $CH(CH_2OH)_2$ and the like. (See, for example, Sovak, M., Editor, *Radiocontrast Aaents*, Springer-Verlag, 1984, pp. 1-125).

The term "aralkyl" refers to an aryl group bonded through an alkyl group.

The term "ether" refers to an alkyl or aryl oxide of the general type $-R-O-R$ where each R is independently alkyl or aryl.

The term "carbocyclic ring" refers to a ring system in which all the ring atoms are carbon, e.g., phenyl or cyclohexyl. The ring may be unsubstituted or substituted by, for example, alkyl, halogen, hydroxy, alkoxy, alkanoyl, alkanoyloxy, amino, alkylamino, dialkylamino, alkanoylamino, thiol, alkylthiol, nitro, cyano, carboxy, carbamoyl, alkoxycarbonyl, alkylsulfonyl, sulfonamido and the like.

The term "halogen" refers to bromo, chloro, fluoro or iodo.

The term "alkanoyl" refers to the group alkyl-C(O)—.

The term "alkanoyloxy" refers to the group alkyl-C(O)—O—.

The term "amino" refers to the group $-NH_2$.

The term "alkylamino" refers to the group —NHR where R is alkyl.

The term "dialkylamino" refers to the group —NRR' where R and R' are each, independently, alkyl.

The term "alkanoylamino" refers to the group alkyl-C(O)—NH—.

The term "thiol" refers to the group —SH.

The term "alkylthiol" refers to the group —SR where R is alkyl.

The term "nitro" refers to the group $-NO_2$.

The term "cyano" refers to the group —CN.

The term "carboxy" refers to the group —C(O)OH or the group —C(O)OR where R is alkyl.

The term "alkoxycarbonyl" refers to the group alkoxy-C—(O)—.

The term "alkylsulfonyl" refers to the group alkyl-$SO_2$—.

The term "sulfonamido" refers to the group $-SO_2NH_2$, the group $-SO_2NHR$ or the group $-SO_2NRR'$ where R and R' are each, independently, alkyl.

The term "carbamoyl" refers to the group —C(O)$NH_2$, the group —C(O)NHR or the group —C(O)NRR' where R and R' are each, independently, alkyl, alkoxy or hydroxyalkyl.

The term "carboxamide" refers to the group —C(O)$NH_2$, the group —C(O)NHR or the group —C(O)NRR' where R and R' are each, independently, alkyl.

The term "acylamino" refers to the group —NH—C(O)—R where R is alkyl.

Preferred compounds of the present invention are those wherein
$R^5$ is

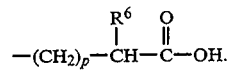

Most preferred are those compounds wherein both $R^1$ and $R^2$ and $R^3$ and $R^4$ form a fused fully saturated cyclohexyl ring, $R^5$ is

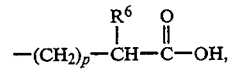

$R^6$ is —H and p is zero.

The compounds of formula I, and salts thereof, may be complexed with a paramagnetic metal atom and used as relaxation enhancement agents for magnetic resonance imaging. These agents, when administered to a mammalian host (e.g., a human) distribute in various concentrations to different tissues, and catalyze relaxation of protons (in the tissues) that have been excited by the absorption of radiofrequency energy from a magnetic resonance imager. This acceleration of the rate of relaxation of the excited protons provides for an image of different contrast when the host is scanned with a magnetic resonance imager. The magnetic resonance imager is used to record images at various times, generally either before and after administration of the agents, or after administration only, and the differences in the images created by the agents' presence in tissues are used in diagnosis. In proton magnetic resonance imaging, paramagnetic metal atoms such as gadolinium-(III), and manganese(II), chromium(III) and iron(III) (all are paramagnetic metal atoms with favorable electronic properties) are preferred as metals complexed by the ligands of formula I. Gadolinium(III) is the most preferred complexed metal due to the fact that it has the highest paramagnetism, it has low toxicity when complexed to a suitable ligand, and it has high lability of coordinated water.

The metal-chelating ligands of the present invention can be complexed with a lanthanide (atomic number 58 to 71) and used as chemical shift agents in magnetic resonance imaging or in magnetic resonance in vivo spectroscopy.

Paramagnetic metal complexes of the present invention are particularly useful as hepatobiliary agents, i.e., for magnetic resonance imaging of the liver and bile ducts.

While the above-described uses for the metal-chelating ligands of the present invention are preferred, those working in the diagnostic arts will appreciate that the ligands can also be complexed with the appropriate metals and used as contrast agents in other imaging techniques such as x-ray imaging, radionuclide imaging and ultrasound imaging, and in radiotherapy.

Use In Imaging

To use the ligands of the present invention for imaging, they are first complexed with an appropriate metal. This may be accomplished by methodology known in the art. For example, the metal can be added to water in the form of an oxide or in the form of a halide or acetate and treated with an equimolar amount of a ligand of the present invention. The ligand can be added as an aqueous solution or suspension. Dilute acid or base can be added (where appropriate) to maintain a suitable pH. Heating at temperatures as high as 100° C. for periods of up to 24 hours or more may sometimes be employed to facilitate complexation, depending on the metal and the chelator, and their concentrations.

Pharmaceutically acceptable salts of the metal complexes of the ligands of this invention are also useful as imaging agents. They can be prepared by using a base (e.g., an alkali metal hydroxide, meglumine, arginine or lysine) to neutralize the above-prepared metal complexes while they are still in solution. Some of the metal complexes are formally uncharged and do not need cations as counterions. Such neutral complexes may be preferred as intravenously administered x-ray and NMR imaging agents over charged complexes because they may provide solutions of greater physiologic tolerance due to their lower osmolality. However, for use as hepatobiliary agents, negatively charged ligands are preferred.

The present invention provides pharmaceutical compositions comprising a compound of formula I, or a salt thereof, optionally complexed with a metal, and a pharmaceutically acceptable vehicle or diluent. The present invention further provides a method for diagnostic imaging comprising the steps of administering to a host a compound of the formula I, or a salt thereof, which is complexed with a metal, and obtaining a diagnostic image, preferably a magnetic resonance image, of said host.

Sterile aqueous solutions of the chelate complexes of the present invention are preferably administered to mammals (e.g., humans) orally, intrathecally and, especially, intravenously in concentrations of 0.003 to 1.0 molar. Use of the metal complexes of the present invention as hepatobiliary agents is preferred. For example, for visualization of the liver, the dose is preferably 0.03 to 0.3 millimole/kilogram. While visualization of the liver and bile ducts is preferred, the metal complexes of the present invention may be employed for visualization of other sites. For example, for the visualization of brain lesions using magnetic resonance imaging, a gadolinium complex of a ligand of formula I may be administered intravenously at a dose of 0.05 to 0.5 millimoles of the complex per kilogram of body weight, preferably at a dose of 0.1 to 0.3 millimoles/kilogram. For visualization of the kidneys, the dose is preferably 0.05 to 0.20 millimoles/kilogram. For visualization of the heart, the dose is preferably 0.05 to 0.3 millimoles/kilogram.

The pH of the formulation of the present metal complexes is preferably between about 6.0 and 8.0, most preferably between about 6.5 and 7.5. Physiologically acceptable buffers (e.g., tris(hydroxymethyl)-aminomethane) and other physiologically acceptable additives (e.g., stabilizers such as parabens) may also be present.

It is also advantageous to employ dual scavenging excipients such as those described in copending application U.S. Ser. No. 032,763, filed Mar. 15, 1993, entitled "DUAL FUNCTIONING EXCIPIENT FOR METAL CHELATE CONTRAST AGENTS", incorporated herein by reference. Those excipients have a general formula corresponding to:

$$D_s[D'(L')]_t$$

wherein D and D' are independently Ca or Zn, L' is an organic ligand which may be different from, or the same as, the ligand employed to complex the metal, and s and t are independently 1, 2 or 3.

The compounds of formula I can be prepared according to the following general scheme:

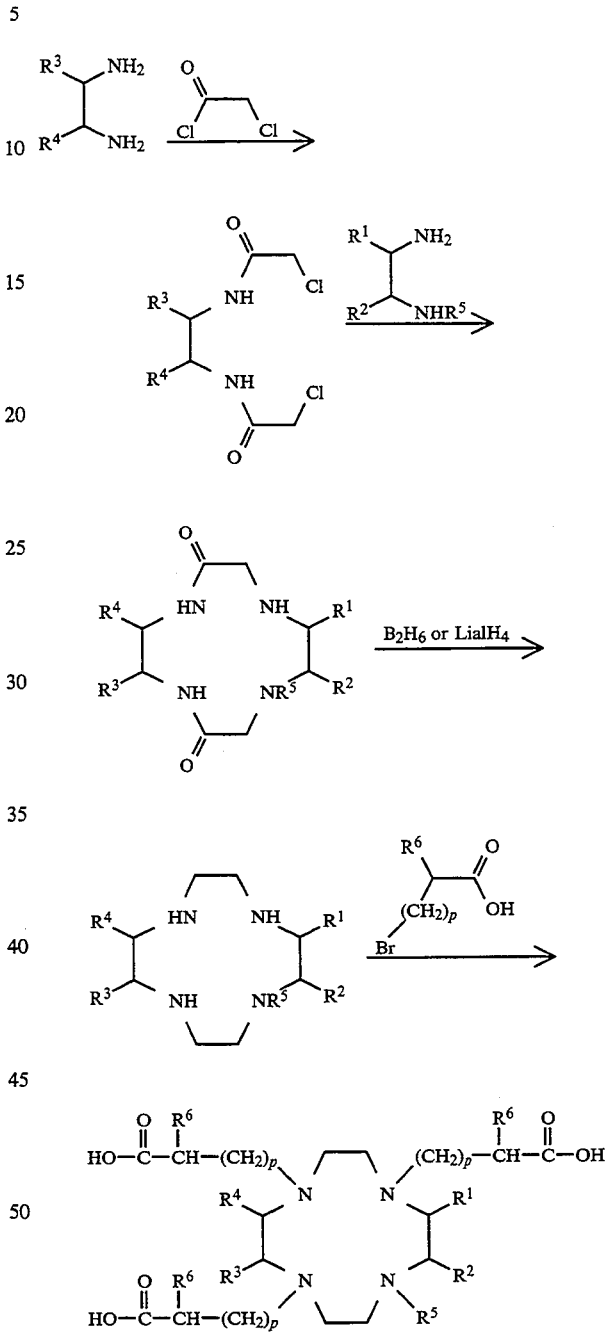

All stereoisomers of the compounds and complexes of the present invention are contemplated herein, whether alone (that is, substantially free of other isomers), in a mixture of certain stereoisomers (for example, as a racemate) or in any other mixture thereof.

The invention will now be further described by the following examples. These examples are illustrative rather than limiting.

EXAMPLE 1

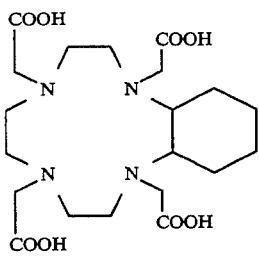

2,5,8,11-Tetracarboxymethyl-2,5,8,11-tetraazabicyclo[10,4,0]hexadecane (A) 4,9-dioxo-2,5,8,11-tetra-azabicyclo[10,4,0]-hexadecane Sodium carbonate (226 g., 2.13 mol.) and trans-1,2-diaminocyclohexane (14.1 ml., 117 mmol.) were added to a solution of N,N'-dichloroacetylethylenediamine (25 g., 117 mmol.) in dry acetonitrile (3.75 l.) under nitrogen. N,N'-dichloroacetylethylenediamine was prepared as reported by Lin W.C., Fiqueira, J. A. D and Alt, H. G. in "New multidentate potential inophors of ether-amide type", Monat. Chem., 1985, 116, 217–221. The reaction mixture was refluxed for 20 hours. The insoluble material formed was filtered off and the volume of the filtrate was reduced to 1 l. by evaporation. Crystals of the compound (A) slowly formed at room temperature. They were collected by filtration and the product was purified by crystallization in acetonitrile. The yield was 7.43 g. of a white solid.

The acetonitrile solution obtained after filtration of compound (A) was concentrated and several fractions of crystallization were collected. The mass spectrum (FAB) and the $^1$H and $^{13}$C NMR spectra of each fraction was recorded and the fractions containing primarily the same compound were combined. Each fraction was crystallized twice from acetonitrile. The fractions obtained at the end of the crystallization process contained the dimeric octaaza and the trimeric dodecaaza monocyclic analogs of compound A.

(B) 2,5,8,11-tetra-azabicyclo[10,4,0]hexadecane

Dried compound (A) (2.54 g., 10 mmol.) was added under nitrogen to a 1M solution of $BH_3$ in tetrahydrofuran (100 ml., 100 mmol.). The reaction mixture was refluxed overnight. After cooling, water was added dropwise until the excess of $BH_3$ was completely eliminated. The resulting suspension was brought to dryness in a rotary evaporator and the remaining solid was added to 140 ml. of a 6M hydrochloric acid solution. The temperature was maintained at 100° C. overnight. Water was eliminated under vacuum and the solid residue was dissolved in a minimum amount of water. LiOH.H$_2$O was added to give a pH adjusted to 12–13. The mixture was extracted three times with methylene chloride. The combined organic fractions were dried (magnesium sulfate), filtered, and evaporated to give 2 g. of compound (B) as a white solid.

(C) 2,5,8,11-tetracarboxymethyl-2,5,8,11-tetraazabicyclo[10,4,0]hexadecane

Bromoacetic acid (11.9 g., 86 mmol.) was dissolved in water (25 ml.). The temperature of the solution was lowered to 5° C. in an ice bath and the acid was neutralized with an aqueous solution of sodium hydroxide (3.43 g., 86 mmol. in 13 ml. water). Compound (B) (3.24 g., 14.3 mmol.) was added to the solution of sodium bromoacetate and the temperature was raised to 70°–80° C. The pH was maintained between 9 and 10 by the dropwise addition of a solution of sodium hydroxide (3.43 g., 86 mmol.) in water (13 ml.). At the end of the addition, the temperature was maintained at 70°–80° C. for 6 hours. The volume of the reaction mixture was then brought down to 40 ml. and the pH was acidified to 3 with 6M hydrochloric acid. An insoluble material formed rapidly. It was filtered and recrystallized in water until no trace of glycolic acid could be found by NMR. A second fraction of the title compound was obtained after further concentration of the reaction mixture. The two fractions were combined and 3.6 g. of the title compound as a white solid was obtained after recrystallization in water. Mass spectrum (FAB): m/e 459 (M+H) and 481 (M+Na).

EXAMPLE 2

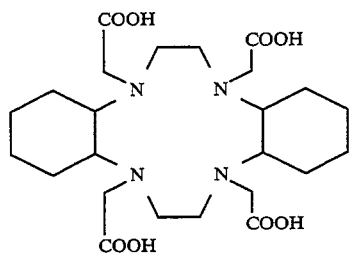

2,5,12,15,-Tetracarboxymethyl2,5,12,15-tetraazatricyclo[14.4.0.0$^{6,11}$]icosane (A) 3,14-dioxo-2,5,12,15-tetraazatricyclo[14.4.0.0$^{6,11}$]icosane N,N'-bis(chloroacetyl)-trans-1,2-diaminocyclohexane was prepared according to the procedure outlined by Saburi, M. and Yoshikawa, S., "Stereochemical studies of N-methyl-(S)-alaninatocobalt(III) complexes with chiral tetraamines. II. Cobalt(III)-N-methyl(S)- and (R)-alaninate-N,N'-bis(β-aminoethyl)-1(R), 2(R)-diaminocyclohexane systems," Bull. Chem. Soc. Jpn., 1974, 47, 1184–1189. Anhydrous sodium carbonate (250 g., 2.36 mol.) was added to a solution of 33.4 g. (125 mmol.) of N,N'-bis(chloroacetyl)-trans-1,2-diaminocyclohexane and 15 ml. (125 mmol.) of trans-1,2diaminocyclohexane in 3750 ml. of acetonitrile. The temperature was raised to 82° C., and the reaction mixture was violently agitated for 20 hours. At the end of the reaction, sodium carbonate was eliminated by filtration and the solvent was evaporated under vacuum. The solid residue was recrystallized from ethanol. Up to five successive batches of the desired compound were obtained after the progressive concentration of the ethanolic solution under vacuum. The yield was 9.6 g. of compound (A) as a white powder.

(B) 2,5,12,15-tetraazatricyclo[14.4.0.0$^{6,11}$]-icosane

A 1M solution of BH$_3$ in tetrahydrofuran (265 ml.) was slowly added to 10.2 g. (33.1 mmol.) of compound (A). The solution was boiled for 24 hours. Water was then added dropwise to destroy the excess BH3 and the reaction mixture was brought to dryness. The solid residue was added to 265 ml. of a 6M hydrochloric acid solution and the mixture was refluxed overnight. Hydrochloric acid was eliminated under vacuum. The residue was digested in ethanol, filtered and dissolved in water. Concentrated ammonia was added until the pH became strongly basic. The inorganic precipitate that formed was filtered off and the filtrate was extracted with methylene chloride yielding 6.3 g. of compound (B) as a white solid after elimination of the solvent.

(C) 2,5,12,15-tetracarboxymethyl-2,5,12,15-tetrazatricyclo[14.4.0.0$^{6,11}$]icosane A suspension in 90 ml. of dried dimethylformamide was prepared by mixing 1.88 g. (6.7 mmol.) of compound (B), 3.72 ml. (33.5 mmol.) of Br—CH$_2$COOC$_2$H$_5$, and 4.63 g. (33.5 mmol.) of potassium carbonate. The mixture was heated at 90° C. under nitrogen for 12 hours. The suspension was filtered and a solution of LiOH.H$_2$O (3.09 g., 73.6 mmol.) in 90 ml. water was added to the filtrate. The mixture was refluxed for 2 hours. The solvent was eliminated under vacuum and the residue was dissolved in a minimum amount of water. The pH was adjusted to 3–4 with concentrated hydrochloric acid and a colorless compound crystallized out. It was easily recrystallized in boiling water. After drying under vacuum, 1.05 g. of the title compound as a white powder was obtained. $^{13}$C NMR (D$_2$O, 320K, strongly acid pH, ppm vs TMS): 174.2, 66.8, 66.6, 58.3, 52.8, 52.1, 49.6, 27.8, 26.9, 26.5. Mass spectrum (FAB): m/e 281 (M+H).

EXAMPLE 3

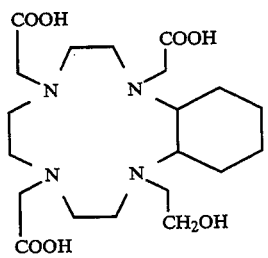

2,5,11-Tricarboxymethyl-8-(2'-hydroxyethyl)-2,5,8,11-tetraazabicyclo[10,4,0]hexadecane (A) 3,10-dioxo-8-(2'-hydroxyethyl)-2,5,8,11-tetraazabicyclo[10,4,0]hexadecane Into a 5 l. erlenmeyer flask containing 5 l. of anhydrous acetonitrile was placed 17.4 g. (65 mmol.) of N,N'-bis(chloroacetyl)-trans-1,2-diaminocyclohexane (see Example 2), 6.8 g. (65 mmol.) of 2-(2-aminoethylamino)ethanol and 130 g. (1.23 mmol.) of sodium carbonate. The reaction mixture was heated at 82° C. under nitrogen for 50 hours. After eliminating sodium carbonate by filtration, acetonitrile was eliminated under vacuum until the volume was reduced to 500 ml. A precipitate formed immediately and the reaction mixture was stirred for several hours at room temperature. The precipitate was filtered off and was washed with a few ml. of acetonitrile and dried under vacuum. 8.2 g. of compound (A) was obtained as a white solid.

(B) 8-(2'-hydroxyethyl)-2,5,8,11-tetraazabicyclo[10,4,0]hexadecane

Into a dry flask under nitrogen was placed 3.00 g. (10 mmol.) of compound (A) and 100 ml. of a 1M solution of BH$_3$.THF in anhydrous tetrahydrofuran. The reaction mixture was refluxed for 12 hours. Water was added dropwise until no reaction was taking place with the excess of BH$_3$.THF. The solvent was stripped off on a rotary evaporator after addition of a few ml. of methanol to avoid excessive foaming. The solid residue was treated with about 10 ml. of a concentrated solution of LiOF.H$_2$O until the pH reached 12–13. This aqueous phase was extracted 6 times with 100 ml. of methylene chloride. The extracts were collected and dried over magnesium sulfate. The solvent was removed under vacuum to yield 2.62 g. of Compound (B) as a white powder that was used in the next step without further purification.

(C) 2,5,11-tricarboxymethyl-8-(2'-hydroxyethyl)-2,5,8,11-tetraazabicyclo[10,4,0]hexadecane To a solution of 3.19 g. (23 mmol.) of bromoacetic acid in 10 ml. of water chilled in an ice bath was added dropwise 0.92 g. (23 mmol.) of sodium hydroxide dissolved in 5 ml. of water while maintaining the temperature below 5° C. This mixture was added to a solution of 1.38 g. (5.1 mmol.) of compound (B) dissolved in 5 ml. of water. The reaction mixture was heated to 70°–80° C. and a solution of 0.92 g. of sodium hydroxide (23 mmol.) in 5 ml. of water was added dropwise while maintaining the pH in the 9–10 range. After completing the addition of sodium hydroxide, the reaction mixture was agitated for 12 additional hours at 70°–80° C. The reaction mixture was allowed to cool to room temperature and the pH was brought to 3 by addition of a 6M hydrochloric acid solution. The solution was applied to a cation exchange resin (H+ form). After washing with water, the macrocyclic ligand was eluted with 0.5M aqueous ammonia. Obtained after rotary evaporation was 1.66 g. of the title compound as the ammonium salt. The acid form was obtained by elution on an anion exchange column (formate form) with 0.5M formic acid. $^{13}$C NMR (D$_{20}$, strongly acid pH, ppm vs TMS): 177.6, 175.4, 170.4, 67.7, 59.9, 57.9, 57.2, 54.9, 53.4, 52.2, 51.9, 49.9, 48.9, 48.3, 26.0–25.6. Mass spectrum (FAB): title compound in the acid form, m/e 445 (M+H).

EXAMPLE 4

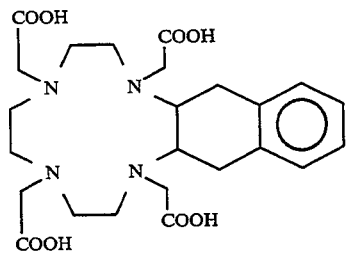

2,5,8,11-Tetracarboxymethyl-14,15-benzo-2,5,8,11-tetraaza-bicyclo[10,4,0]hexadecane (A) 4,9-dioxo-14,15-benzo-2,5,8,11-tetraazabicyclo[10,4,0]hexadecane Trans-2,3-diamino-1,2,3,4-tetrahydronaphthalene was prepared as reported by Yano, T., Kobayashi, H. and Ueno, K., "Stereospecific syntheses and acid dissociation of 2,3-diaminotetralins and 2,3-diamino-trans-decalins", Bull. Chem. Soc. Jpn., 1973 46, 985–990. In a 2 l. flask equipped with a mechanical stirrer and a refluxed condenser were placed 5.38 g. (33.16 mmol.) of trans-2,3-diamino-1,2,3,4-tetrahydronaphthalene and 1 l. of anhydrous acetonitrile. N,N'-dichloroacetylethylenediamine (7.06 g., 33.16 mmol.) and 64 g. (0.60 mol.) of anhydrous sodium carbonate were added to the solution. After 20 hours at 90° C., the reaction mixture was filtered and the filtrate was evaporated until the volume was reduced to 500 ml. A precipitate formed slowly when the solution was allowed to stand at room temperature overnight. It was filtered off and dried under vacuum. The yield was 5.52 g. of a brownish powder. Compound (A) was isolated by adding the powder to 500 ml. of water at 50° C. A brown viscous oil did not dissolve and was eliminated by filtration. The remaining aqueous solution was concentrated under vacuum until white crystals were formed. After letting the solution stand overnight at room temperature, 3.73 g. of compound (A) were collected by filtration. The reaction mixture left after isolation of compound (A) was concentrated further by evaporation of the acetonitrile but it yielded only the dimeric form, m.p. 230°–231° C.

(B) 14,15-benzo-2,5,8,11-tetraaza-bicyclo[10,4,0]hexadecane

The reduction of compound (A) was accomplished by adding 1.5 g. (4.96 mmol) under a nitrogen sparge to 50 ml. of a 1M solution of BH$_3$.THF in dry tetrahydrofuran. The reaction mixture was left boiling for 12 hours. The reaction mixture was chilled in an ice bath and water was slowly added until the generation of hydrogen could no longer be observed. The solvent was removed on a rotary evaporator and the remaining solid was suspended in 50 ml. of 6M hydrochloric acid. The reaction mixture was refluxed overnight. The volatiles were removed on a rotary evaporator. The excess of hydrochloric acid was eliminated by dissolving the remaining solid in water and by evaporating the solution under reduced pressure. This procedure had to be repeated three times. The solid residue obtained after the elimination of the hydrochloric acid in excess was dissolved in 30 ml. of water, and a concentrated solution of LiOH.H$_2$O was added until the pH reached 12–13. The solution was extracted with 200 ml. of dichloromethane. The organic phase was separated by decantation and was dried (magnesium sulfate), filtered and evaporated to give 1.06 g. of a yellowish vitreous solid. An analytically pure sample was obtained by recrystallization of the tetraamine as the hydrochloride salt.

(C) 2,5,8,11-tetracarboxymethyl-14,15-benzo2,5,8,11-tetraaza-bicyclo[10,4,0]hexadecane Bromoacetic acid (7.14 g., 51.4 mmol.) was dissolved in 20 ml. of water and was slowly neutralized by the dropwise addition of a solution of 2.05 g. (51.2 mmol.) of sodium hydroxide in 10 ml. of water while maintaining the temperature below 5° C. The reaction mixture was added to a solution of 2.35 g. (8.57 mmol.) of compound (B) in 10 ml. of water. The temperature was raised to 70°–80° C. and the pH was maintained between 9 and 10 by the dropwise addition of an aqueous solution of sodium hydroxide (2.05 g., 51.42 mmol. in 10 ml. of water). The addition of sodium hydroxide was completed after 5 hours and the reaction mixture was left at 70°–80° C. overnight. After cooling, the volume of the reaction mixture was reduced to 45 ml. on a rotary evaporator and a 6M solution of hydrochloric acid was added dropwise until the pH was lowered to 3. A beige precipitate (3.5 g.) formed immediately. It was collected by filtration, recrystallized in water (colorless needles) and dried under vacuum. $^{13}$C NMR (D$_2$O, strongly basic medium, ppm vs TMS): 182.2, 182.1, 161.9, 161.8, 140.9, 140.3, 129.9, 129.5, 128.8, 128.2, 64.0, 60.7, 59.9, 58.1, 57.3, 56.1, 55.1, 54.9, 51.0, 50.6, 50.4, 46.6, 28.4. Mass spectrum (FAB): m/e 507 (M+H).

EXAMPLE 5

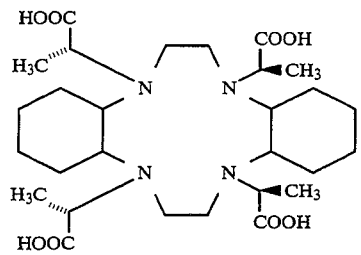

α,α′,α″,α‴-Tetramethyl-eicosahydroibenzo[b,h][1,4,7,10]tetraazacyclododecane-5,8,13,16-tetraacetic acid (A) N,N′-(1,2-Cyclohexylene)-bis-(2-chloroacetamide, A solution of 1,2-diaminocyclohexane (100 g., 0.88 mole) in methylene chloride (875 ml.) was cooled to 5° C. in an ice bath. The reaction mixture was treated concurrently with 1) a solution of chloroacetyl chloride (298 g., 2.64 mmol) in methylene chloride (1050 ml.), and 2) a solution of potassium carbonate (279 g., 2.02 mol.) in water (280 ml.), dropwise. After the addition was complete, the reaction mixture was stirred an additional 2 hours at ambient temperature. The reaction mixture was filtered. This reaction was repeated on the same scale. The solid remaining after filtration was combined with the above sample, and both were washed with 2×1000 ml. ice-cold water to afford 278 g. (60%) of compound (A) as a white solid.

(B) Eicosahydrodibenzo[b,h][1,4,7,10]tetraazacyclododecan-6,15-dione

A solution of trans-1,2-diaminocyclohexane (15 ml., 125 mmol.) and compound (A) (33.4 g., 125 mmol.) in acetonitrile (3000 ml.) was treated with sodium carbonate (250 g., 2.36 mmol.) and the mixture was heated to reflux under nitrogen. The progress of the reaction was monitored by HPLC by noting the disappearance of starting materials along with the formation of a new peak corresponding to the desired product. The reaction was cooled to ambient temperature, and filtered to remove sodium carbonate. This solution was concentrated in vacuo to afford crude product which was recrystallized from absolute ethanol to afford 9.2 g. (24%) of the trans-syn-trans isomer, compound (B), as a white solid with a melting point of 251°–271° C.

(C) Eicosahydrodibenzo[b,h][1,4,7,10]tetraazacyclododecane

A suspension of compound (B) (5.1 g., 16.5 mmol.) in freshly distilled tetrahydrofuran (250 ml.) was cooled to 0° C. under nitrogen, and treated dropwise with a solution of diborane in tetrahydrofuran (1M, 132 ml., 132 mmol.). After the addition was complete, the reaction mixture was heated to reflux under nitrogen overnight. After 24 hours, the reaction mixture was cooled to 0° C., and the excess diborane was destroyed by the dropwise addition of 20% water in tetrahydrofuran (about 100 ml.). The solvent was removed in vacuo. The residue was treated with 132 ml. of 6N hydrochloric acid, and heated to reflux overnight. The mixture was concentrated to dryness in vacuo. The residue was taken up in water and adjusted to pH 12.5 with concentrated sodium hydroxide. This material was extracted with methylene chloride and concentrated in vacuo to afford 3.4 g. (74%) of desired compound (C) as a white solid.

(D) (L)-Benzyl-2-Triflyloxypropionate

A solution of L-benzyl lactate (7.95 g., 44.1 mmol.) and pyridine (3.66 g., 46.3 mmol.) in methylene chloride (40 ml.) at 0° C. under nitrogen was treated with triflic anhydride (12.44 g., 44.1 mmol.) dropwise, via syringe. After 20 hours, silica gel TLC run in hexanes:methylene chloride (1:1, v/v) indicated formation of a single spot, as well as disappearance of the starting lactate. The pyridinium triflate was filtered, and the filtrate was concentrated in vacuo to afford crude product. This material was flashed on 200 g. of silica gel, eluting with hexanes: methylene chloride (2:1, v/v). The product-containing fractions were pooled to afford 5.4 g. (39%) of compound (D) as a colorless, light oil.

(E) Eicosahydrodibenzo [b,h][1,4,7,10]tetraazacyclo-dodecane-5,8,13,16-tetraacetic acid, tetrakis-5,8,13,16(benzyloxycarbonyl)methyl ester A solution of compound (C) (1.37 g., 4.91 mmol.) in acetonitrile (25 ml.) under nitrogen was treated with powdered potassium carbonate (3.38 g., 24.5 mmol.). The reaction mixture was treated with compound (D) (6.75 g., 21.6 mmol.), dropwise, via syringe. After 22 hours, the reaction mixture was diluted with 50 ml. of acetonitrile and filtered. The filtrate was concentrated in vacuo. The residue was suspended in 100 ml. of water, and extracted with 4×100 ml. of methylene chloride. The organic extracts were dried (magnesium sulfate) and concentrated in vacuo to afford 4.6 g. (101%) of product as a light, pale yellow oil. This material was flash chromatographed in 450 g. of silica gel, eluting with 4 liters of hexanes:ethyl acetate (3:1, v/v), followed by 2 liters of hexanes: ethyl acetate (1:1, v/v). The product-containing fractions were pooled to afford 1.62 g. (35%) of compound (E) as a viscous, pale yellow oil.

(F) $\alpha,\alpha',\alpha'',\alpha'''$-Tetramethyl-eicosahydrodibenzo[b,h][1,4,7,10]tetraazacyclo-dodecane-5,8,13,16-tetraacetic acid A solution of compound (E) in methanol (6 ml.) and 2M aqueous hydrochloric acid (2.5 ml.) was treated with 10% Pd/C (wet, Degussa type), and the reaction mixture was subjected to a steady stream of hydrogen gas at 1 atmosphere. After 22 hours, the reaction mixture was filtered through Celite ®, and washed with 2M aqueous hydrochloric acid. The filtrate was concentrated in vacuo and lyophilized from water to afford 870 mg. (73%) of .4 hydrochloric acid salt. This material was combined with 75 mg. of previous crude product from an identical preparation, and the resulting solid was dissolved in 100 ml. of water. This solution was adjusted to pH 7.5 with concentrated ammonium hydroxide. The resulting solution was applied to a 2.5×45 cm column of AG1-X2 (formate form) anion exchange resin, and eluted with water to remove inorganic salts. The compound was eluted with a gradient from 2000 ml. of water to 2000 ml. of 0.2N formic acid. Two separate fractions were collected and lyophilized: Fraction 1: 425 mg. (40% of theoretical), HPLC purity (see below)=99.4%; Fraction 2: 100 mg. (10% of theoretical), HPLC purity=94.8%.

HPLC: Retention time=8.39 min., purity=99.4%; Conditions: Column: PRP-X-100 5μ-100° A, 250×4.6 mm i.d.; Solvent: CH₃CN/50 mM phosphate buffer, pH 6.2 (1:4, v/v); Flow rate: 1.0 ml/minute; Detection: UV @ 220 nm. IR: (KBr) 2942 and 2866 (CH stretching), 1723 and 1623 (C=O) cm¹. Mass Spectrum: (FAB) 569+ (M+H)+, 523+ (M+H−COOH)+, 497+ (M+H−CH(CH₃)COOH)+. Anal. calc'd. for $C_{28}H_{48}N_4O_8$. 2.56 water (614.8): C, 54.70; H, 8.71; N, 9.11; O, 27.48. Found: C, 54.31; H, 8.94; N, 8.91.

EXAMPLE 6

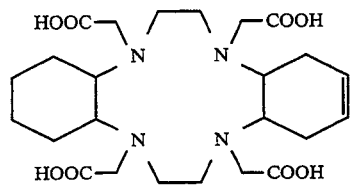

1,2,3,4,4a,5,6,7,8,8a,9,12,12a,13,14,15,16,16a-Octadecahydrodibenzo[b,h][1,4,7,10]-tetraazacylododecin-5,8,13,16-tetraacetic acid

(A) trans-4-Cyclohexene-1,2-diamine dihydrochloride

In an oven-dried 2-neck, round-bottomed flask equipped with a Dewar condenser and septum, a stirred solution of freshly distilled fumaryl dichloride (13.0 ml., 110 mmol.) in dry ethyl ether (50 ml.) was cooled to −50° C. under a dry nitrogen atmosphere. Condensed butadiene (40 ml.) was added via cannula to the solution, and the reaction mixture was allowed to warm to room temperature. The solution was allowed to reflux spontaneously for 3 hours, after which the excess butadiene and ethyl ether were removed in vacuo. The colorless oil was dissolved in dry 1,4-dioxane (50 ml.) and the solution was treated with azidotrimethylsilane (34 ml., 250 mmol.). Nitrogen evolution was initiated using an 80–°85° C. oil bath and the reaction mixture was heated at 105° C overnight. The solution was cooled to room temperature, diluted with acetone (75 ml.), and cautiously treated with concentrated hydrochloric acid (35 ml.). The hydrochloric acid salt of the diamine was collected by filtration and was washed with acetone and ethyl ether. 14.4 g. (64.69%) of compound (A) was obtained as a white powder.

(B) N,N'-(1,2-Cyclohexylene)-bis-(2-chloroacetamide)

A solution of 1,2-diaminocyclohexane (50.0 g., 438 mmol.) in methylene chloride (438 ml.) was cooled to 0°–5° C. and vigorously stirred with a mechanical stirrer. To it was concurrently added solutions of chloroacetyl chloride (105 ml., 1.28 mmol.) in methylene chloride (430 ml.) and potassium carbonate (139.5 g., 1.01 mol.) in water (279 ml.) over a period of 4 hours, and the resultant mixture was stirred at room temperature overnight. The suspension was filtered and the solid was thoroughly washed with ice-cold water to remove potassium carbonate. The layers in the filtrate were separated and the organic layer was concentrated to near dryness. The mixture was filtered and the solid was treated as before. The recovered solids were combined and dried in a vacuum oven at 50° C. over phosphorus pentoxide. The yield of compound (B) was 109.77 g. (93.84%) as a white solid.

(C) 1,2,3,4,4a,5,6,7,8,8a,9,12,12a,13,14,15,-16,16a-Octadecahydrodibenzo[b,h][1,4,7,10]-tetraazacyclododecin-6,15-dione A suspension containg compound (B) (33.4 g., 125 mmol), compound (A) (23.1 g., 125 mmol., hydrochloride salt) and anhydrous sodium carbonate (250 g. , 2.36 mmol. ) in acetonitrile (3750 ml. ) was vigorously stirred and refluxed for 26 hours. After cooling, sodium carbonate was removed by filtration and the filtrate was evaporated to dryness under reduced pressure. The solid residue (22.1 g.) was recrystallized from ethanol (150 ml.) and afforded 7.95 g. of a material which contained two isomers. A single, pure isomer (1.28 g.) was obtained by a second recrystallization step. The original mother liquor furnished 1.97 g. more of the isomeric material. The mother liquor from the second crystallization was dried under vacuum and combined with the second crop of crystals. A portion of the material (3.22 g.) was purified by silica gel chromatography using methylene chloride:methanol (4:1 v/v) as the eluant to afford an additional 2.104 (65% recovery) of the pure product. The yield was 9.92 g. (26%) of the mixed isomer product.

(D) 1,2,3,4,4a,5,6,7,8,8a,9,12,12a,13,14,15,-16,16a-Octadecahydrodibenzo[b,h][1,4,7,10]-tetraazacyclo-dodecin-trihydrochloride A mixture containing compound (C) (3.45 g., 11.3 mmol.) and 1M L/A/H$_4$ (40ml.) in tetrahydrofuran (100 ml.) was refluxed for 21 hours under a dry nitrogen atmosphere. The solution was cooled and the excess LAH was decomposed by the careful addition of a saturated aqueous solution of Rochelles's salt (10 ml.). Absolute ethanol (50 ml.) was added to the suspension and the mixture was refluxed overnight. After filtration, the residual product in the filter cake was extracted by treatment of the solid with hot ethanol (2×100 ml.). The filtrates were combined and evaporated to afford 4.0 g. of a brownish mass. Crystallization from acetonitrile gave off-white crystals which dissolved in ethyl ether and hexane washes. A portion of this material (400 mg., 1.6 mmol.) was converted to the hydrochloride salt by treatment with methanolic hydrochloric acid (7 ml.).

(E) 1,2,3,4,4a,5,6,7,8,8a,9,12,12a,13,14,15,-16,16a-Octadecahydrodibenzo[b,h][1,4,7,10]-tetraazacyclodo-decin-5,8,13,16-tetraacetic acid A mixture containing crude compound (D) (1.05 g., 3.77 mmol.), anhydrous potassium carbonate (2.61 g., 18.8 mmol.) and t-butyl bromoacetate (3.23 g., 16.6 mmol.) was heated at 50°–55° C. overnight under a dry nitrogen atmosphere. After cooling, the reaction mixture was diluted with acetonitrile (10 ml.), filtered, and the filter cake was washed with an additional 10 ml. of acetonitrile. The filtrates were combined and evaporated under reduced pressure. The residue was suspended in water (25 ml.) and was extracted with methylene chloride (4×10 ml.). The organic layer was washed with brine (40 ml.), dried over magnesium sulfate, and evaporated to dryness to afford 2.35 g. of crude tetraester. Deprotection of the crude tetraester was accomplished by overnight treatment of the ester with anisole (12 ml.) and TFA (100 ml.) under a dry nitrogen atmosphere. The TFA was removed in vacuo and the residue was repeatedly dissolved in water and concentrated under reduced pressure until the solution was free of cloudiness. The crude product (2.0 g.) was dissolved in water (50 ml.), neutralized to pH 7.0 and purified by AG-1 (1.5×30 cm, formate) anion exchange chromatography. The column was washed with a linear gradient of formic acid (0 to 0.2N formic acid, 2 l. each), and the product was eluted at approximately 0.05N formic acid. The fractions containg pure product were combined, evaporated to dryness, dissolved in water and lyophilized to afford 541 mg. (45%) of the title compound as a fluffy white material.

HPLC: Column: PRPX-100, 5μ, 250×4.6 mm. Conditions: 20% CH$_3$CN in 50 mM NaH$_2$PO$_4$ (pH 6.2); flowrate: 1.0 ml./min.; detector: UV at 220 nm.; t$_r$=7.31 minutes. IR (KBr,cm$^{-1}$): 2940 (CH stretching); 1717 (C=O stretching); 1636 (C=C stretching). MS(PPINCI NH$_3$/dep 100, m/z): 511 (M+H)$^+$. Anal. calc'd. for C$_{24}$H$_{38}$N$_4$O$_8$.2.28 H$_2$O: C, 52.26; H, 7.78; N, 10.16; O, 29.81 Found: C, 52.27; H, 7.84; N, 10.01; H$_2$O, 7.44% (desorption KF).

EXAMPLE 7

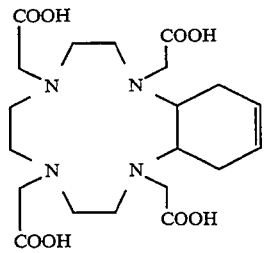

2,5,8,11-Tetracarboxymethyl-2,5,8,11-tetraaza-bicyclo[10,4,0]hexadec-14ene (A) 4,9-dioxo-2,5,8,11-tetraaza-bicyclo[10,4,0]hexadec-14-ene The synthesis of trans-4-cyclohexene-1,2-diamine has been reported by Witiak et al. (J. Med. Chem. 1987, 30, 1327–1336). Trans-4-cyclohexene-1,2-diamine (9.25 g., 82.5 mmol.) and N,N'-dichloroacethylenediamine (17.55 g., 82.5 mmol.) were dissolved in 2700 ml. of acetonitrile. Anhydrous sodium carbonate (158 g., 1.5 mol.) was added to the solution and the mixture was refluxed for 23 hours. After cooling, the insoluble salt was filtered off and the filtrate was brought to dryness. The solid residue was recrystallized in about 20 ml, of hot ethanol.

Melting point: 203°–205° C.

(B) 2,5,8,11-bicyclo[10,4,0]hexadec-14-ene

Compound (A) (0.8 g., 3.17 mmol.) was added under nitrogen to 100 ml. of diglyme that had been dried and distilled over lithium aluminum hydride. The compound solubilized when the temperature was increased. Lithium aluminum hydride (3.91 g., 0.1 mol.) was added to the warm solution and the temperature was brought to 100° C. The reaction mixture was agitated for 15 days. After cooling, excess hydride was destroyed by the careful addition of ethyl acetate and water. The insoluble material was filtered off and washed with water and ethanol. The solvents were eliminated under vacuum at 80° C. The residue was dissolved in hydrochloric acid 6M and the solution was brought to dryness on a rotary evaporator. The residue was added to about 20 ml. of ethanol. The suspension was refluxed for one hour and then kept overnight at 4° C. The precipitate was filtered and dried under vacuum. The free amine was obtained by adding the hydrochloride to trichloromethane and saturated with dry ammonia. The suspension was agitated overnight and the insoluble ammonium chloride was filtered off. The solvent was eliminated and 0.57 g. of a viscous liquid remained.

Mass spectrum: (FAB, sample in 3-nitrobenzyl alcohol): m/e 225 (M+H)

(C) 2,5,8,11-tetracarboxymethyl-2,5,8,11-tetraaza-bicyclo[10,4,0]hexadec-14-ene

Bromoacetic acid (0.63 g., 4.5 mol.) was dissolved in water and was slowly neutralized below 5° C. with an aqueous solution of sodium hydroxide (0.18 g., 4.55 mmol., in 2 ml. of water). This solution was added to a solution of compound (B) (0.17 g., 0.76 mmol.) in 3 ml.

of water. The reaction mixture was heated at 70°-80° C. and a solution of sodium hydroxide (0.18 g., 4.55 mmol., in 2 ml. of water) was added dropwise over 5 hours so as to maintain the pH between 9 and 10. The agitation was continued overnight at 80° C. The pH was lowered to 3 with concentrated hydrochloric acid and the reaction mixture was slowly concentrated under a stream of air. The title compound easily formed crystals and was recrystallized in a small volume of water.

Yield: 45%, 0.15 g. $^{13}$C NMR (in D$_2$O, protonated form): 177.6, 177.0, 173.0, 172.8, 127.5, 124.7, 64.5, 58.4, 57.3, 57.0, 55.7, 53.6, 52.5, 52.4, 50.2, 48.8, 47.6, 26.0, 25.4 Mass spectrum (sample in 3-nitrobenzyl alcohol): m/e 479 (M+Na), 501 (M−H+2 Na).

EXAMPLE 8

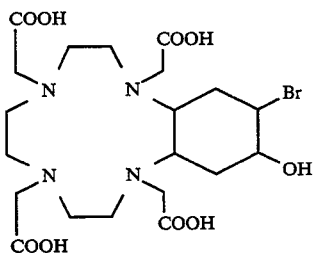

2,5,8,11-Tetracarboxymethyl-16(14)-bromo-14(16)-hydroxy-2,5,8,11-tetraazabicyclo[10,4,0]hexadecane The dihydrochloride of the compound of Example 7 (0.2 g., 0.38 mmol.) was dissolved in 4 ml. of water and the pH was adjusted to 6. N-bromosuccinimide (0.07 g., 0.38 mmol.) was added to this solution at 10° C. The reaction mixture was stirred at 10° C. for one hour until N-bromosuccinimide was totally dissolved. The clear solution was kept overnight at 4° C. The solvent was stripped off in a rotary evaporator and in the dark. The solid residue was dissolved in a minimum amount of methanol, and acetone was added until the solution became slightly cloudy. The compound was left to crystallize overnight at 4° C., and was collected by filtration in the dark.

Yield: 0.07 g., 45% $^{13}$C NMR (in D$_2$O, protonated form): 179.2, 178.6, 173.1, 172.5, 71.6, 63.2, 62.8, 58.5, 58.4, 57.2, 56.7, 56.0, 53.7, 52.9, 52.6, 51.7, 50.2, 49.4, 48.0, 47.7, 29.2, 28.9, 27.8, 27.1 Mass spectrum: (sample in 3-nitrobenzyl alcohol): m/e 575 and 577 (M+Na), 597 and 599 (M−H+2 Na).

EXAMPLE 9

Gadolinium (III) complexes of the ligands reported in Examples 1-8

All gadolinium (III) complexes were prepared by adjusting the pH of a stoichiometric mixture of gadolinium trichloride and one of the ligands reported in Examples 1-8 in water. The complexation reactions were started at about pH 3 and the solutions were heated to 60° C. for about 10 minutes before each addition of a few drops of a diluted aqueous solution of sodium hydroxide. The addition of sodium hydroxide was stopped when the pH reached 6.5. The complexation reactions were completed in a minimum of 3 to 4 hours and often require one full day. Each solution was concentrated and the products were purified by preparative HPLC. Evaporation of the appropriate fractions yielded colorless solids.

What is claimed is:
1. A compound of the formula:

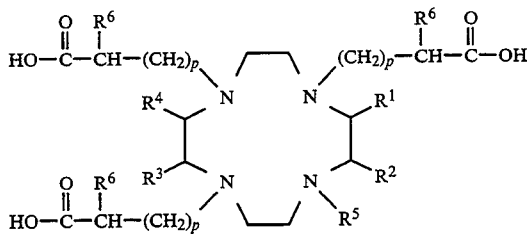

wherein
$R^1$ and $R^2$ and $R^3$ and $R^4$ independently form, together with the carbon atoms in the tetraazacyclododecane macrocycle to which they are attached, a fused fully or partially saturated nonaromatic cyclohexyl ring which may be unsubstituted or substituted by one or more halogen, alkyl, ether, hydroxy or hydroxyalkyl groups, and which may be further fused to a carbocyclic ring, or $R^1$ and $R^2$ are each hydrogen and $R^3$ and $R^4$ form a fused fully or partially saturated non-aromatic cyclohexyl ring as defined above, or $R^1$ and $R^2$ form a fused fully or partially saturated non-aromatic cyclohexyl ring as defined above and $R^3$ and $R^4$ are hydrogen;
$R^5$ is

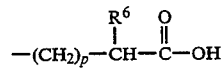

or hydrogen, alkyl, aralkyl, aryl, alkoxy, hydroxyalkyl,

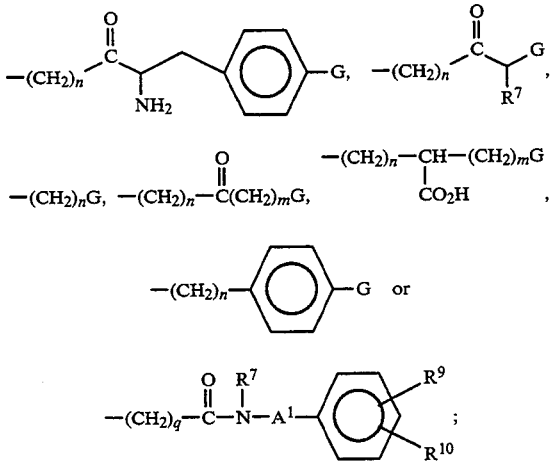

$A^1$ is —(CH$_2$)$_q$—, —(CH═CH)—, —(CH═CH)$_2$— or a single bond; each —(CH$_2$)$_q$— may be independently substituted with alkyl or hydroxyalkyl;
$R^6$ is hydrogen or alkyl;
$R^7$ is hydrogen, hydroxyalkyl, alkoxy, alkyl, aryl or aralkyl;
G is —NH$_2$, —NCS,

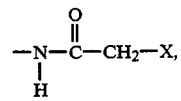

—CO$_2$H, —NHR$^8$, —N(R$^8$)$_2$ or —CN;

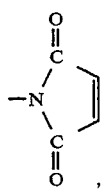

R$^8$ is alkyl, hydroxyalkyl,

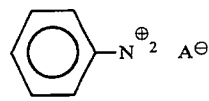

(where A is an anion),

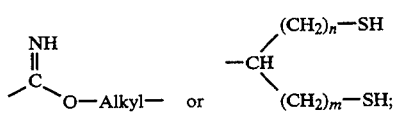

R$^9$ and R$^{10}$ are each independently hydrogen, alkyl, —NO$_2$, —NH$_2$,

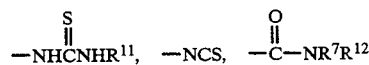

or —NR$^7$COR$^6$;

R$^{11}$ is hydrogen, alkyl or hydroxyalkyl;
R$^{12}$ is hydrogen, hydroxyalkyl, alkoxy, alkyl, aryl or aralkyl;
X is chloro, bromo or iodo;
m and n are each independently zero or an integer from one to five;
p is zero or one; and
q is an integer from 1 to 5;
or a salt thereof.

2. A compound of claim 1 wherein R$^1$ and R$^2$ are each hydrogen and R$^3$ and R$^4$ form a fused fully or partially saturated non-aromatic cyclohexyl ring which may be unsubstituted or substituted by one or more halogen, alkyl, ether, hydroxy or hydroxyalkyl groups, and which may be further fused to a carbocyclic ring.

3. A compound of claim 1 wherein R$^3$ and R$^4$ are each hydrogen and R$^1$ and R$^2$ form a fused fully or partially saturated non-aromatic cyclohexyl ring which may be unsubstituted or substituted by one or more halogen, alkyl, ether, hydroxy or hydroxyalkyl groups, and which may be further fused to a carbocyclic ring.

4. A compound of claim 1 wherein R$^1$ and R$^2$ and R$^3$ and R$^4$ independently form a fused fully or partially saturated non-aromatic cyclohexyl ring which may be unsubstituted or substituted by one or more halogen, alkyl, ether, hydroxy or hydroxyalkyl groups, and which may be further fused to a carbocyclic ring.

5. A compound of claim 1 wherein R$^5$ is

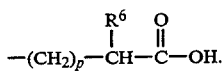

6. A compound of claim 1 wherein both R$^1$ and R$^2$, and R$^3$ and R$^4$, form a fused fully saturated cyclohexyl ring, R$^5$ is

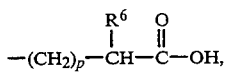

R$^6$ is —H and p is zero.

7. A compound of claim 1 selected from the group consisting of 2,5,8,11-Tetracarboxymethyl-2,5,8,11-tetraaza-bicyclo[10,4,0]hexadecane; 2,5,12,15-Tetracarboxymethyl-2,5,12,15-tetraazatricyclo[14.4.0.0$^{6,11}$]icosane; 2,5,11-Tricarboxymethyl-8-(2'-hydroxyethyl)-2,5,8,11-tetraazabicyclo[10,4,0]hexadecane; 2,5,8,11-Tetracarboxymethyl-14,15-benzo-2,5,8,11-tetraazabicyclo[10,4,0]hexadecane; Eicosahydrodibenzo[b,h][1,4,7,10]tetraazacyclododecane-5,8,13,16-tetraacetic acid; 1,2,3,4,4a,5,6,7,8,8a,9,12,12a,13,14,15,16,16a-Octadecahydrodibenzo[b,h]][1,4,7,10]-teraazacyclododecin-5,8,13,16-tetraacetic acid; 2,5,8,11-Tetracarboxymethyl-2,5,8,11-tetraazabicyclo[10,4,0]hexadec-14-ene; and 2,5,8,11-Tetracarboxymethyl-16(14)-bromo-14(16)-hydroxy-2,5,8,11-tetraazabicyclo[10,4,0]hexadecane.

8. A metal chelate comprising a compound of claim 1 complexed with a metal atom.

9. The chelate of claim 8 wherein the metal is selected from atoms having an atomic number of 21 to 29, 42, 44, or 57 to 83.

10. The chelate of claim 8 wherein said metal is gadolinium.

11. A method for diagnostic imaging comprising the steps of administering to a host a compound of claim 1, which compound is complexed with a metal, and obtaining a diagnostic image of said host.

12. The method of claim 11 wherein R$^1$ and R$^2$ are each hydrogen and R$^3$ and R$^4$ form a fused fully or partially saturated non-aromatic cyclohexyl ring which may be unsubstituted or substituted by one or more halogen, alkyl, ether, hydroxy or hydroxyalkyl groups, and which may be further fused to a carbocyclic ring.

13. The method of claim 11 wherein R$^3$ and R$^4$ are each hydrogen and R$^1$ and R$^2$ form a fused fully or partially saturated non-aromatic cyclohexyl ring which may be unsubstituted or substituted by one or more halogen, alkyl, ether, hydroxy or hydroxyalkyl groups, and which may be further fused to a carbocyclic ring.

14. The method of claim 11 wherein R$^1$ and R$^2$ and R$^3$ and R$^4$ independently form a fused fully or partially saturated non-aromatic cyclohexyl ring which may be unsubstituted or substituted by one or more halogen, alkyl, ether, hydroxy or hydroxyalkyl groups, and which may be further fused to a carbocyclic ring.

15. The method of claim 11 wherein R$^5$ in said compound is

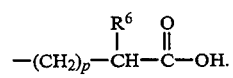

16. The method of claim 11 wherein both R$^1$ and R$^2$ and R$^3$ and R$^4$ form a fused fully saturated cyclohexyl ring R$^5$ is

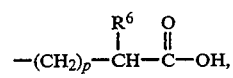

R$^6$ is —H and p is zero in said compound.

17. The method of claim 11 wherein the compound is selected from the group consisting of 2,5,8,11-Tetracarboxymethyl-2,5,8,11-tetraazabicyclo[10,4,0]hexadecane; 2,5,12,15-Tetracarboxymethyl-2,5,12,15-tetraazatricyclo[14.4.0.0$^{6,11}$]icosane; 2,5,11-Tricarboxymethyl-8-(2'-hydroxyethyl)-2,5,8,11-tetraazabicyclo[10,4,0]hexadecane; 2,5,8,11-Tetracarboxymethyl-14,15-benzo-2,5,8,11-tetraazabicyclo[10,4,0]hexadecane; Eicosahydrodibenzo[b,h][1,4,7,10]tetraazacyclododecane-5,8,13,16-tetraacetic acid; 1,2,3,4,4a,5,6,7,8,8a,9,12,12a,13,14,15,16,16a-Octadecahydrodibenzo[b,h][1,4,7,10]-tetraazacyclododecin-5,8,13,16-tetraacetic acid; 2,5,8,11-Tetracarboxymethyl-2,5,8,11-tetraazabicyclo[10,4,0]hexadec-14-ene; and 2,5,8,11-Tetracarboxymethyl-16(14)-bromo-14(16)-hydroxy-2,5,8,11-tetraazabicyclo[10,4,0]hexadecane.

18. The method of claim 11 wherein said image is a magnetic resonance image.

19. The method of claim 18 wherein said metal is gadolinium and said image comprises an image of the hepatobiliary system of said host.

20. A pharmaceutical composition comprising a compound of claim 1, optionally complexed with a metal, and a pharmaceutically acceptable vehicle or diluent.

* * * * *